United States Patent [19]

König et al.

[11] Patent Number: 5,705,672
[45] Date of Patent: Jan. 6, 1998

[54] TERTIARY AMINES HAVING CARBONATE AND URETHANE GROUPS

[75] Inventors: Klaus König, Odenthal; Ulrich Liman, Langenfeld; Josef Sanders, Leverkusen, all of Germany

[73] Assignee: Bayer Aktiengesellschaft, Leverkusen, Germany

[21] Appl. No.: 510,830

[22] Filed: Aug. 3, 1995

[30] Foreign Application Priority Data

Aug. 9, 1994 [DE] Germany .................. 44 28 108.0

[51] Int. Cl.⁶ ............................................ C07C 271/00
[52] U.S. Cl. ................................... 558/267; 558/276
[58] Field of Search ............................. 558/267, 276

[56] References Cited

U.S. PATENT DOCUMENTS 2,390,551  12/1945  Muskat et al. ................ 558/276 X
2,887,452   5/1959  Alpert et al. .................. 558/267 X

FOREIGN PATENT DOCUMENTS 2052048  3/1992  Canada.

*Primary Examiner*—Richard L. Raymond
*Attorney, Agent, or Firm*—Joseph C. Gil; Lyndanne M. Whalen

[57] ABSTRACT

Tertiary amines having carbonate and urethane groups and optionally hydroxyl groups are produced by reacting a) a polyhydric alcohol and b) a primary-tertiary diamine with c) a carbonic acid derivative selected from the group consisting of optionally cyclic carbonates, urea, phosgene and bis-chlorocarbonates of alcohols of the same type as those used as component a). This reaction may be carried out in one or two steps. The tertiary amines produced by this process are useful as catalysts, which may optionally be incorporated into an isocyanate-reactive material, in the isocyanate addition reaction for the production of polyurethane plastics. These tertiary amines are particularly useful for the production of foam backed plastic films.

8 Claims, No Drawings

TERTIARY AMINES HAVING CARBONATE AND URETHANE GROUPS

BACKGROUND OF THE INVENTION

The present invention relates to a process for the production of novel tertiary amines having carbonate and urethane groups and optionally hydroxyl groups which are useful as catalysts in the production of polyurethane plastics, particularly in the production of composites.

DE-OS 4,030,515 describes the production of urethanes having tertiary amino groups by reacting cyclic carbonates (e.g., ethylene carbonate or propylene carbonate) and amines having both primary and tertiary amino groups, and the use of these urethanes as catalysts for the production of polyurethanes. The resulting urethanes are catalytically active and possess hydroxyl groups which make it possible to incorporate them into the polyurethane matrix. However, as has since been shown by subsequent investigations, complete incorporation of these urethanes is not always guaranteed or has not yet occurred at the beginning of the polyaddition. Due to their low molecular weight, these catalytic urethanes and other catalysts capable of incorporation (e.g. alkoxylated amines) may be released in the surrounding atmosphere and contribute to so-called "fogging". In addition, when these catalysts are used to produce composites (e.g., by foam-backing of plastics films), there is a risk of the catalyst diffusing into the covering material and, under the possible influence of sunlight and heat, damaging the covering material.

SUMMARY OF THE INVENTION

It is an object of the present invention to provide a process for the production of novel tertiary amines containing both carbonate and urethane groups.

It is another object of the present invention to provide new tertiary amine catalysts for the production of polyurethanes.

It is a further object of the present invention to provide tertiary amine catalysts which have a lower tendency to diffuse out of foams produced with those catalysts.

It is also an object of the present invention to provide a process for producing tertiary amine catalysts containing urethane and carbonate groups.

It is another object of the present invention to provide a process for the production of polyurethanes in which a tertiary amine containing urethane and carbonate groups is used as the catalyst.

These and other objects which will be apparent to those skilled in the art are accomplished by reacting a polyol corresponding to a specified formula and an amine corresponding to a specified formula with a carbonic acid derivative selected from a specified group. These materials are reacted in quantities such that the molar ratio of hydroxyl groups from the polyol to the primary amino groups of the amine is from about 4:1 to about 16:1. The carbonic acid derivative is used in an amount of 0.5 moles carbonic acid derivative plus from about 0.2 to about 0.5 moles carbonic acid derivative for each mole of hydroxyl groups from the polyol.

DETAILED DESCRIPTION OF THE PRESENT INVENTION

The present invention relates to a process for the production of tertiary amines having carbonate and urethane groups, and optionally hydroxyl groups. In this process, a) a polyol component made up of at least one polyhydric alcohol represented by the formula $$Q(OH)_n \quad (I)$$

and b) an amine component having at least one primary-tertiary diamine represented by the formula

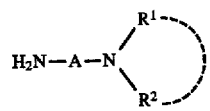
(II)

are reacted with c) a carbonic acid derivative selected from the group consisting of 1) carbonates corresponding to the formula

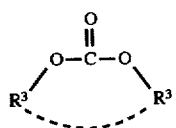
(III)

2) urea, 3) phosgene and 4) bis-chlorocarbonates of the polyols of Formula (I), in one or two steps to form carbonate and urethane groups. The reactants are used in quantities such that the ratio of components a) and b) corresponds to a molar ratio of hydroxyl groups to primary amino groups of from about 4:1 to about 16:1. The carbonic acid derivative c) is used in a quantity such that there are 0.5 moles of carbonic acid derivative c) for each mole of amine b) plus from about 0.2 to about 0.5 moles of carbonic acid derivative for each mole of hydroxyl groups of polyol a).

In the above Formulae (I), (II) and (III), Q, A, $R^1$, $R^2$, $R^3$ and n have the following meanings:

Q represents a residue obtained by removal of n-hydroxyl groups from an n-hydric aliphatic alcohol, optionally having ether groups, having a molecular weight in the range of from about 90 to about 400, n represents an 2 or 3, A represents a divalent, aliphatic hydrocarbon residue having 2 to 6 carbon atoms in which at least 2 carbon atoms are present between the nitrogen atoms which appear in Formula (II), $R^1$ and $R^2$, which may be the same or different, each represents an alkyl residue having from 1 to 4 carbon atoms or together with the nitrogen atom and optionally, further heteroatoms, form a saturated, heterocyclic 5- or 6-membered ring which is inert with respect to the carbonic acid derivatives c), and $R^3$ individually represents a phenyl residue or an alkyl residue having from 1 to 4 carbon atoms or together form an alkylene residue with 2 or 3 carbon atoms.

The present invention also relates to the tertiary amines having carbonate and urethane groups and optionally hydroxyl groups which are obtained by this process and to the use of these tertiary amines as catalysts in the production of polyurethane plastics by the isocyanate polyaddition process (particularly, the production of composites by the foam-backing of plastics films with a reaction mixture that forms a polyurethane foam).

The products of the process of the present invention generally have a carbonate group content (calculated as $CO_3$, molecular weight=60) of from about 5 to about 30% by weight, a urethane group content (calculated as $CHNO_2$, molecular weight=59) of from about 5 to about 20% by weight, an alcoholic hydroxyl group content of from about 0 to about 10% by weight and a tertiary amino group content (calculated as N, atomic weight=14) of from about 1 to about 5% by weight.

The starting materials which are typically used in the process of the present invention are a) dihydric or trihydric polyols, b) primary-tertiary diamines and c) carbonic acid derivatives.

The polyol component a) is at least one polyol represented by Formula (I). Examples of polyols which are suitable for use as component a) include: (i) aliphatic diols, optionally having ether groups and having a molecular weight in the range of from about 90 to about 400, preferably from about 106 to about 250; (ii) aliphatic triols, optionally having ether groups, and having a molecular weight in the range of from about 120 to about 400, preferably from about 134 to about 400 and (iii) any mixtures of dihydric and trihydric alcohols (i) and (ii).

Specific examples of suitable dihydric alcohols (i) include: 1,4-butanediol; 1,5-pentanediol; 3-methyl-1,5-pentanediol; 2,2,4-trimethyl-1,6-hexanediol; isomeric heptanediols; isomeric octanediols; isomeric nonanediols; isomeric decanediols; and the known addition products of ethylene oxide and/or propylene oxide to such alcohols or to ethylene glycol or propylene glycol having molecular weights of from about 90 to about 400. Di-, tri- and tetra-ethylene glycol, and di-, tri- and tetra-propylene glycol and their mixtures are preferred. It is possible to influence the hydrophilicity or the solubility of the finished products in water or polyether polyol via the ethylene oxide or propylene oxide portion.

Examples of suitable trihydric polyols (ii) include: trimethylolethane, trimethylolpropane and known addition products of ethylene oxide and/or propylene oxide to such triols having molecular weights of from about 90 to about 400. It is possible to influence the hydrophilicity or solubility in water or polyether polyol of the finished products via the ethylene oxide or propylene oxide portion. The preferred polyhydric alcohol (ii) is trimethylolpropane.

Suitable primary-tertiary amines b) are those represented by Formula (II). Those amines in which A represents an alkylene residue with 2 to 4 carbon atoms and $R^1$ and $R^2$ each represent methyl groups are particularly preferred.

The primary-tertiary diamines may be produced by alkylation of mono-protected diprimary amines (e.g., aminoalkyl phthalimides) and subsequent hydrolysis or hydrazinolysis. They may also be produced by the addition of aziridine or acrylonitrile to secondary amines such as dimethylamine, diethylamine, dipropylamine, piperidine or morpholine and subsequent hydrogenation of the cyanoethylated amines. Specific examples of suitable primary-tertiary amines b) include: 1-(dimethylamino)-3-aminopropane, 1-(diethylamino)-3-aminopropane, 1-(di-n-propylamino)-3-aminopropane, 1-(dimethylamino)-2-methyl-3-aminopropane, 1-(dimethylamino)-4-amino-butane, 1-(dimethylamino)-5-aminopentane, N-(2-aminoethyl)morpholine, N-(3-aminopropyl)morpholine, N-(2-aminoethyl)piperidine and N-(3-amino-propyl)piperidine. It is also possible to use mixtures of the amines listed. 1-(dimethylamino)-3-aminopropane is preferred.

The carbonic acid derivatives c) are compounds which react with alcohols to form carbonates or with alcohols and primary amines to form urethanes. Suitable carbonic acid derivatives are those selected from the group consisting of optionally cyclic carbonates represented by Formula (III), urea, phosgene and bis-chlorocarbonates of polyols represented by Formula (I). The polyol used as component a) and the polyol represented by Formula (I) from which the bis-chlorocarbonate is formed need not be the same. In the process of the present invention, optionally cyclic carbonates corresponding to Formula (III) are preferably used as the carbonic acid derivative c). Specific examples of suitable carbonates corresponding to Formula (III) are dimethyl, diethyl, di-n-propyl, di-n-butyl, diphenyl, ethylene and propylene carbonates. Diphenyl carbonate is particularly preferred.

In carrying out the process of the present invention, the reactants are used in amounts such that the molar ratio of hydroxyl groups to primary amino groups is from about 4:1 to about 16:1, about 0.5 moles of carbonic acid derivative are present for each mole of primary-tertiary amine and from about 0.2 to about 0.5 moles of carbonic acid derivative are present for each mole of hydroxyl groups in polyol a).

The process of the present invention may be carried out in one or two steps.

The process of the present invention may, for example, be carried out in one step by homogenizing the polyhydroxyl compound a) and the carbonic acid derivative c) (optionally, after melting at approximately 50° to 80° C.) before the amine component b) is added with stirring. A water-jet vacuum is then applied and the temperature is increased to approximately 110° to 140° C. until distillation of the hydroxyl component of the starting carbonic acid derivative begins. In accordance with the rate of distillation, the internal temperature is gradually increased to a final maximum of 200° C. and is left there until the distillation is completed. Final traces of volatile components may be removed by applying a high vacuum or by azeotropic destillation adding small amounts of ethylene glycol, water or steam.

In this one-step method, a maximum of 0.5 moles of carbonic acid derivative, i.e. preferably carbonate, is used for each equivalent of hydroxyl groups of polyol component a) and for each mole of amine b). Because the condensation reaction proceeds more slowly towards the end of the reaction when equivalent quantities of carbonic acid derivative c) and total hydroxyl component a) plus amine component b) are used, it may be advantageous to use a deficiency (based on the quantity of hydroxyl compound and amine component) of carbonic acid derivative. However, it should in principle be ensured that the ratios of the starting materials are selected so that reaction products having carbonate group, urethane group, hydroxyl group and tertiary amino group contents within the above-specified ranges are obtained.

The reaction which occurs in the process of the present invention is preferably carried out without the use of solvents. However, solvents may in some cases be useful or necessary (e.g., when using starting materials which are only slightly soluble). In such cases, solvents which do not react with the reaction components and which have a boiling point below the boiling point of the hydroxyl component of the carbonic acid derivative used allow total separation by distillation. Hydrocarbons such as toluene or xylene; halogenated hydrocarbons such as chlorobenzene or dichlorobenzene; ethers such as ethylene glycol dimethyl ether, diethylene glycol dimethyl ether, diphenyl ether and dioxane; and amides such as dimethylformamide, dimethylacetamide and N-methylpyrrolidone are examples of suitable solvents. In some cases, the addition of a catalyst such as an alkali-base or a transition metal compound such as dibutyltin oxide or tetrabutyl titanate may be advantageous. However, it is preferred that no additional catalyst be used.

When carrying out the process of the present invention in two steps, a polycarbonate is initially prepared from polyol component a) and carbonic acid derivative c) by any of the known processes in the first step. It is preferred that the molar ratio of hydroxyl groups of component a) to carbonic acid derivative c) be maintained in the range of from about 2:1 to about 3:1. The polycarbonate is then reacted with amine b) in the sense of an aminolysis reaction of the carbonate groups. Reaction of a polyhydric alcohol with a diaryl carbonate to form a polycarbonate is described, e.g., in DOS 2,555,805. Similar reactions with dialkyl carbonates (DOS 2,555,805), with cyclic carbonates or dioxolanones (DOS 1,915,908), with phosgene (DOS 1,595,446), with bis-chlorocarbonates (DP 857,948) and with urea (P. Ball, H. Fuillmann and W. Heitz, Angew. Chem. 92 (1980), part 9, p. 742, 743) are also known. The molecular weight $M_n$ of the polycarbonates should be as high as possible in order to have sufficient carbonate groups available for reaction with amine component b). Average molecular weights $M_n$ of 1000 to 4000 are preferred. The polycarbonate intermediates obtained are subsequently reacted with amine component b). The quantity of amine component b) is calculated so that from about 0.2 to about 0.5 moles of amine component b) are available for each mole of carbonate groups. The polycarbonate/amine reaction may be carried out by adding amine component b) with stirring to the polycarbonate which may be molten or may be at ambient temperature or at an elevated temperature of from about 60° to about 80° C. Stirring may then be continued at 80° to 120° C. until the primary amino groups of the amine component have reacted. The degree to which the primary amino groups have reacted can be readily determined by, e.g., titration with HCl or perchloric acid.

The second step of this two-step embodiment of the process of the present invention is preferably carried out without solvents. However, solvents may in some cases be useful or even necessary (e.g., when only slightly soluble starting materials are used). When a solvent is used, a solvent which does not react with the reaction components is preferred. The solvents listed above as being suitable for the one-step method of carrying out the process of the present invention are among those which would be suitable for this two-step embodiment of the present invention.

The type and amount of the starting materials used in the two-step embodiment of the process of the present invention are selected so that the product tertiary amine will have a carbonate group content of from about 5 to about 30% by weight, a urethane group content of from about 5 to about 20% by weight, a tertiary amino group content of from about 1 to about 5% by weight and a hydroxyl group content of from about 0 to about 10% by weight.

The tertiary amines produced by the process of the present invention are largely odorless. By selection of suitable starting materials, particularly the hydroxyl compounds a), products which display excellent compatibility with the polyether polyols commonly used in polyurethane chemistry are obtained. These tertiary amines may therefore be used advantageously as catalysts or activators for the production of polyurethanes, particularly for the production of polyurethane foams from the commonly used starting materials.

The tertiary amines produced in accordance with the present invention are generally included in foam-forming mixtures in quantities of from about 1 to about 20% by weight, based on the total polyurethane foam-forming reaction mixture. These tertiary amines are generally used as auxiliaries in addition to the conventional polyhydroxyl compounds (particularly polyether polyols) and optionally, in addition to incorporated water, as reactants for the organic polyisocyanate. The amount of tertiary amine compound of the present invention used in the production of polyurethane foams is preferably selected so that from about 0.01 to about 1% by weight tertiary nitrogen atoms are present in the reaction mixture. The amino compounds of the present invention are particularly suitable as catalysts in the production of composites by applying a foam-forming reaction mixture to a plastic film and allowing that mixture to react to form a foam backing on the plastics film.

The tertiary amines produced in accordance with the present invention may also be used as surface-active agents (in amine form or in the form of their ammonium salts), emulsifiers or as stabilizers.

Having thus described our invention, the following Examples are given as being illustrative thereof. All percentages given in these Examples are percentages by weight.

EXAMPLES

Production of Starting Materials

Polycarbonate A 3686 g (19.2 moles) of tripropylene glycol, 858 g (6.4 moles) of trimethylolpropane, 4794 g (22.4 moles) of diphenyl carbonate and 2 g of dibutyltin oxide were gradually heated to 180° C. at 12 mbar, during which process phenol distilled off. When nothing else distilled off at 180° C./12 mbar, stirring was continued for an additional 2 hours at 160° C. on an oil pump at 0.5 mbar to remove residual phenol.

| | |
|---|---|
| OH number: | 136 |
| Molecular weight $M_n$: | 1650 g |
| Viscosity/25° C.: | 55,740 mPa · s |

Polycarbonate B 2894 g (21.6 moles) of dipropylene glycol, 965 g (7.2 moles) of trimethylolpropane, 5393 g (25.2 moles) of diphenyl carbonate and 5 g of dibutyltin oxide were reacted in accordance with the same procedure as was used to produce POLYCARBONATE A.

| | |
|---|---|
| OH number: | 162 |
| Molecular weight $M_n$: | 1385 g |
| Viscosity/25° C.: | 117,920 mPa · s |

Polycarbonate C 3725 g (19.2 moles) of triethylene glycol, 858 g (6.4 moles) of trimethylolpropane, 4794 g (22.4 moles) of diphenyl carbonate and 2 g of dibutyltin oxide were reacted in accordance with the procedure described above for the preparation of POLYCARBONATE A.

| | |
|---|---|
| OH number: | 129.2 |
| Molecular weight $M_n$: | 1737 |
| Viscosity/25° C.: | 22,560 mPa · s |

Example 1 (One-step Reaction)

1188 g (7.92 moles) of triethylene glycol and 2080 g (9.72 moles) of diphenyl carbonate were melted at 80° C. under nitrogen. To this mixture was added 367 g (3.6 moles) of 1-(dimethylamino)-3-aminopropane dropwise, stirring, over a period of approximately 1 hour. A water-jet vacuum was then applied and the internal temperature was increased to 160° C, during which process phenol distilled off. When nothing else distilled off at 160° C./12 mbar, stirring was continued for an additional 2 hours at 160° C. on an oil pump at 0.5 mbar to remove residual phenol. The product had the following characteristics:

| Viscosity/25° C.: | 1,960 mPa · s |
| Carbonate groups: | 22.6% |
| Urethane groups: | 13.1% |
| Hydroxyl groups: | 0% |
| tertiary nitrogen: | 2.8% |

Example 2 (One-step Reaction)

1286 g (6.70 moles) of tripropylene glycol, 299 g (2.23 moles) of trimethylolpropane, 1673 g (7.82 moles) of diphenyl carbonate and 341 g (3.35 moles) of 1-(dimethylamino)-3-aminopropane were reacted in accordance with the same procedure used in Example 1. The product had the following characteristics:

| Viscosity/25° C.: | 4,430 mPa · s |
| Carbonate groups: | 12.6% |
| Urethane groups: | 9.28% |
| Hydroxyl groups: | 6.25% |
| tertiary nitrogen: | 2.2% |

Example 3 (Two-step Reaction)

267 g (2.62 moles) of 1-(dimethylamino)-3-aminopropane was rapidly added dropwise to 1400 g of POLYCARBONATE A at 50° C. in a nitrogen atmosphere, stirring well. Stirring was continued for an initial 2 hours at 100° C. and then an additional 5 hours at 120° C. The product obtained had the following characteristics:

| Viscosity/25° C.: | 4,320 mPa · s |
| Carbonate groups: | 12.6% |
| Urethane groups: | 9.27% |
| Hydroxyl groups: | 6.24% |
| tertiary nitrogen: | 2.2% |

Example 4 (Two-step Reaction)

640 g of POLYCARBONATE B and 286 g (2.62 moles) of 1-(dimethylamino)-3-aminopropane were reacted in accordance with the procedure described in Example 3. The characteristics of the product obtained were as follows:

| Viscosity/25° C.: | 4,100 mPa · s |
| Carbonate groups: | 6.16% |
| Urethane groups: | 16.7% |
| Hydroxyl groups: | 8.48% |
| tertiary nitrogen: | 3.96% |

Example 5 (Two-step Reaction)

700 g of POLYCARBONATE B and 243 g (1.674 moles) of N,N-bis-(3-aminopropyl)-methylamine were reacted in accordance with the procedure described in Example 3. The characteristics of the product obtained were as follows:

| Viscosity/25° C.: | 1,140 mPa · s |
| Carbonate groups: | 14.2% |
| Urethane groups: | 10.5% |
| Hydroxyl groups: | 7.04% |
| tertiary nitrogen: | 2.49% |

Example 6 (Two-step Reaction)

1400 g of POLYCARBONATE B and 456 g (4.47 moles) of 1-(dimethylamino)-3-aminopropane were reacted in accordance with the procedure described in Example 3. The characteristics of the product obtained were as follows:

| Viscosity/25° C.: | 6,320 mPa · s |
| Carbonate groups: | 10.83% |
| Urethane groups: | 14.2% |
| Hydroxyl groups: | 8.18% |
| tertiary nitrogen: | 3.37% |

Example 7 (Two-step Reaction)

1400 g of POLYCARBONATE C and 354 g (3.47 moles) of 1-(dimethylamino)-3-aminopropane were reacted in accordance with the procedure described in Example 3. The characteristics of the product obtained were as follows:

| Viscosity/75° C.: | 60 mPa · s |
| Carbonate groups: | 8.89% |
| Urethane groups: | 11.67% |
| Hydroxyl groups: | 6.73% |
| tertiary nitrogen: | 2.77% |

EXAMPLES OF APPLICATIONS

Polyol formulation 48 parts by weight of a polyether polyol with an OH number of 28, produced by propoxylation of trimethylolpropane and subsequent ethoxylation of the propoxylation product (PO:EO weight ratio=82.5:17.5), and 44 parts by weight of a polyether polyol with an OH number of 28 built up in the same way on propylene glycol were blended with the quantity of activator indicated in Table 1 in each of the parallel tests reported in Table 1. 2.5 parts by weight water were added as blowing agent.

Polyisocyanate Component

In each of the following Examples, the polyisocyanate used was a mixture from the diphenylmethane series (mixtures of diisocyanatophenylmethane isomers and their higher homologs) having a viscosity (23° C.) of 200 mPa·s and an NCO content of 32% by weight.

Production of Foams

Foams were produced by the manual foaming method in each of the Examples reported in Table 1. In this process, all of the components, with the exception of the polyisocyanate component, were pre-stirred for 30 s (stirring speed: 1000 rpm). The isocyanate component was then added and stirring was continued for an additional 10 s at ambient temperature. The mixture ratio corresponded to an isocyanate index of 100.

The reactivity of the polyol component was determined in parallel tests from the cream time, rise time, flow time and setting time. The polyol formulation was combined with the polyisocyanate component in a beaker at ambient temperature with stirring. The cream time is the time which passed from the moment the polyisocyanate was added to the beginning of the foaming process. The rise time is the time which passed from the moment the polyisocyanate was added to the end of the foaming process. The setting time was the time which passed from the moment the polyisocyanate was added until the foam is tack-free. The flow time is calculated from the difference between rise time and cream time. The relative density is the density calculated after cutting off the foam cap in a 660 ml beaker.

| Activator | Cream time(s) | Rise time(s) | Flow time(s) | Setting time(s) | Relative density (g/l) | Parts by weight |
|---|---|---|---|---|---|---|
| Example 1 | 14 | 150 | 136 | 172 | 58 | 3.0 |
| Example 3 | 15 | 125 | 115 | — | 56 | 3.0 |
| Example 6 | 13 | 85 | 72 | 95 | 53 | 3.0 |
| Example 7 | 14 | 92 | 78 | 105 | 55 | 3.0 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a tertiary amine having carbonate and urethane groups comprising reacting a) a polyol represented by the formula $$Q(OH)_n \quad (I)$$

in which

Q represents the residue obtained by removing n-hydroxyl groups from an n-hydric aliphatic alcohol having a molecular weight in the range from 90 to 400, and n represents 2 or 3, and b) an amine corresponding to the formula

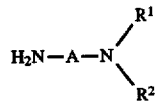

(II)

in which

A represents the residue of a divalent, aliphatic hydrocarbon having from 2 to 6 carbon atoms in which at least 2 carbon atoms are present between the nitrogen atoms which appear in Formula (II), $R^1$ and $R^2$ which may be the same or different, each represents an alkyl residue having from 1 to 4 carbon atoms or together with the nitrogen atom to which each is bonded form a saturated heterocyclic 5- or 6-membered ring which heterocyclic ring is inert with respect to carbonic acid derivatives, with c) a carbonic acid derivative selected from the group consisting of 1) carbonates corresponding to the formula

(III)

in which $R^3$ each represents a phenyl residue, an alkyl residue having from 1 to 4 carbon atoms or together form an alkylene residue having 2 or 3 carbon atoms, 2) urea, 3) phosgene and 4) bis-chlorocarbonates of polyols represented by Formula (I), in amounts such that the molar ratio of hydroxyl groups from a) to primary amino groups of b) is from about 4:1 to about 16:1, and a total of about 0.5 moles of carbonic acid derivative c) plus from about 0.2 to about 0.5 moles of carbonic acid derivative c) for each mole of hydroxyl groups in a) to form carbonate and urethane groups.

2. The process of claim 1 in which the residue represented by Q includes ether groups.

3. The process of claim 1 in which a polycarbonate having hydroxyl groups is produced by reacting polyol a) with carbonic acid derivative c) before the amine b) is added.

4. The process of claim 3 in which a molar ratio of hydroxyl groups of a) to carbonic acid derivative c) is from about 2:1 to about 3:1.

5. The process of claim 3 in which the polycarbonate having hydroxyl groups is reacted with amine b) to form urethane groups.

6. The process of claim 5 in which the molar ratio of primary amino groups of b) to carbonate groups of the polycarbonate with hydroxyl groups is maintained at from about 0.2:1 to about 0.5:1.

7. The tertiary amine produced by the process of claim 1.

8. The tertiary amine produced by the process of claim 6.

* * * * *